United States Patent [19]
Solari

[11] 4,229,837
[45] Oct. 28, 1980

[54] SAFETY GOGGLES

[76] Inventor: Ray L. Solari, 1670 Cordova St., Los Angeles, Calif. 90007

[21] Appl. No.: 790,479

[22] Filed: Apr. 25, 1977

[51] Int. Cl.² .............................................. A61F 9/02
[52] U.S. Cl. ......................................... 2/431; 2/433; 2/439
[58] Field of Search ....................... 2/431, 433, 439, 9, 2/10

[56] References Cited

U.S. PATENT DOCUMENTS

| 427,438 | 5/1890 | McConihay | 2/431 |
|---|---|---|---|
| 1,351,491 | 8/1920 | Schwabacher | 2/433 X |
| 2,281,152 | 4/1942 | Hollingsworth | 2/9 |
| 2,914,769 | 12/1959 | Anderson | 2/9 |
| 3,934,271 | 1/1976 | Rhee | 2/9 X |
| 4,031,564 | 6/1977 | Wood | 2/9 |

FOREIGN PATENT DOCUMENTS

| 133723 | 8/1949 | Australia | 2/433 |
|---|---|---|---|
| 484408 | 7/1917 | France | 2/433 |
| 866887 | 9/1941 | France | 2/433 |
| 626217 | 10/1961 | Italy | 2/433 |
| 622302 | 4/1949 | United Kingdom | 2/433 |
| 847365 | 9/1960 | United Kingdom | 2/433 |

Primary Examiner—Peter P. Nerbun
Attorney, Agent, or Firm—George J. Netter

[57] ABSTRACT

Goggle-like apparatus includes horizontal eye openings with vertically elongated opening wall extensions in front of the eye. In one version, the frame parts are notched with the intervening portions facing toward each other. In another version, the inwardly directed portions of the frame are formed to extend outwardly and away from the face of the wearer. In a different aspect, the goggle frames are of an undulating construction and at least one rod-like (or wire-like) element extends vertically across the central area of view of the wearer, one for each eye, the ends of which are affixed in the opposite frames.

3 Claims, 14 Drawing Figures

SAFETY GOGGLES

The present invention relates generally to safety goggles, and, more particularly, to safety goggles especially adaptable for use in sporting activities.

1. Field of the Invention

In a number of sporting activities, such as tennis, handball, squash, racquet ball, basketball, soccer, and the like, there is the ever present danger of a participant being struck in the eye by the ball, a racquet or hand of his opponent, resulting in injury. It is, therefore, manifest that the use of some means for protecting the eyes from such injury would be advisable.

2. Prior Art

In the past there have been a variety of different types of protective devices worn by participants in such sports, generally in the form of goggles or glasses and all of these known eye protective apparatus suffer from one or more deficiencies. For example, certain of the protective apparatus have been heavy and cumbersome to wear, causing the wearer a measure of discomfort while participating in the sport, and are therefore undesirable, if only from that standpoint. Other known apparatus of a goggle-like construction and covering the eye region with a transparent means, substantially reduces the visibility of the wearer to the point of interference with performance in the sport.

SUMMARY OF THE INVENTION

In the practice of the present invention there are provided goggle-like apparatus to be worn by the sport participant, including horizontally elongated open regions immediately adjacent each eye. Moreover, these open regions each include vertically elongated opening wall extensions in front of the eye. All of the openings are so dimensioned as to prevent the game ball of the sport from extending therethrough. The goggle frame parts defining the openings may include a plurality of openings therein to improve visibility.

In another version, the frame parts defining the eye openings are notched with the intervening portions facing toward each other. In a still further version, the inwardly directed portions of the frame are formed to extend outwardly and away from the face of the wearer.

In a different aspect, the goggle frames are formed into an undulating construction, thereby providing periodic and spaced supporting regions which contact the head and face portions of the wearer, with the intervening spaces extending outwardly away from the head of the wearer to provide protective contact members to intercept the ball, racquet or the like and prevent it from striking the eye region of the wearer. At least one rod-like element extends vertically across the central area of view of the wearer, one for each eye, the ends of which are affixed in the opposite frames. In this latter aspect, by locating the rod-like elements in front of the eye, protection is received against a ball or the like coming into contact with the eye of the wearer and yet little, if any, restriction of visibility results.

DESCRIPTION OF PREFERRED EMBODIMENTS

Figure 1:
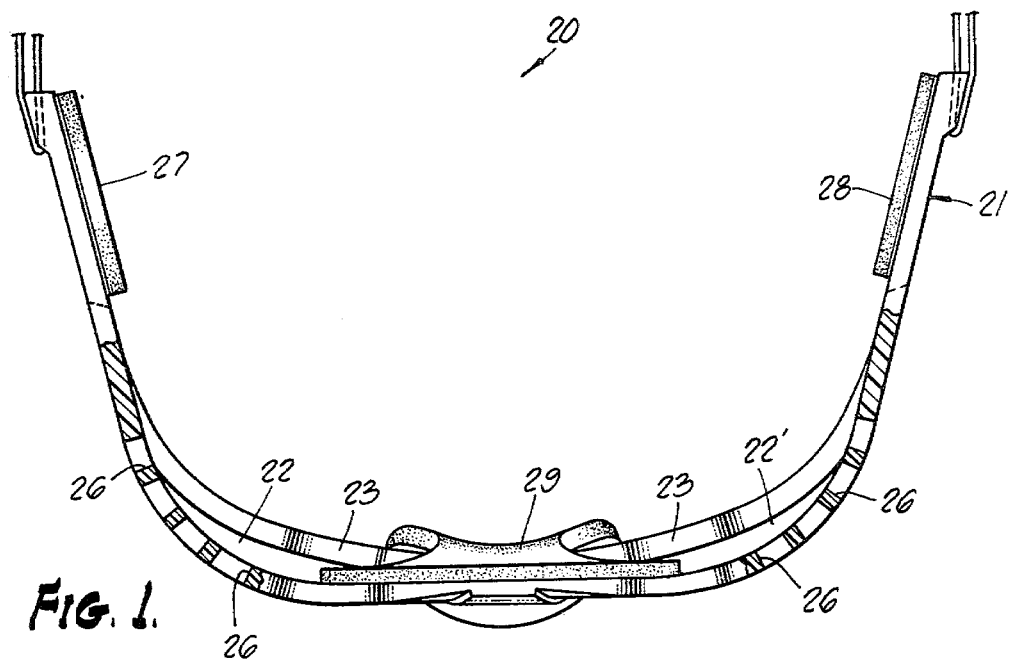
FIG. 1 is a perspective, partially sectional view of one embodiment of safety goggles in accordance with this invention.
Figure 2:
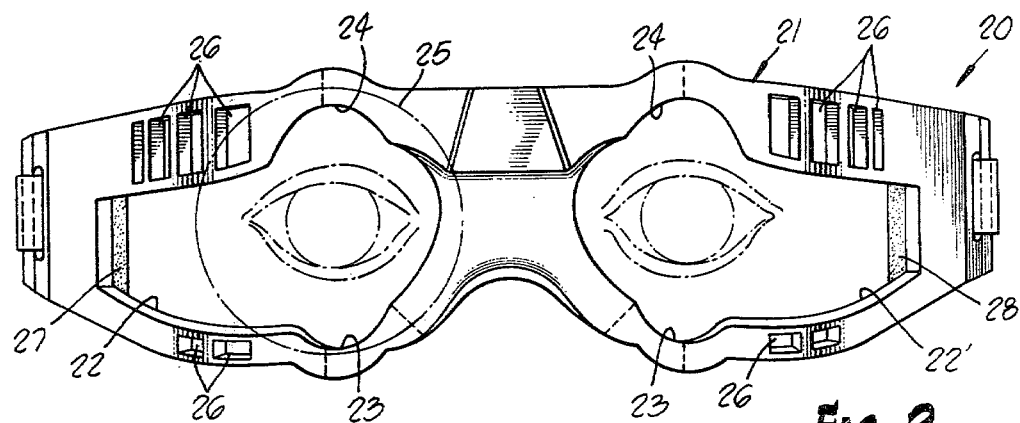
FIG. 2 is a front elevational view of the safety goggles of FIG. 1.
Figure 3:
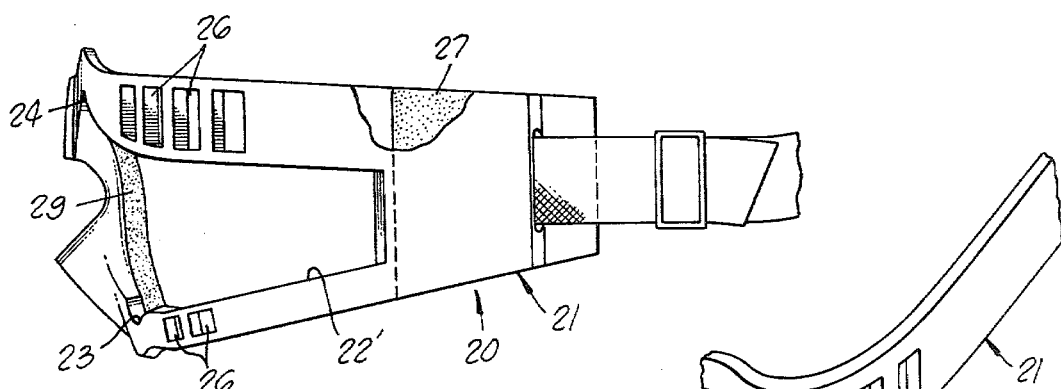
FIG. 3 is an end elevational view of the goggles of FIGS. 1 and 2.

With reference now to the drawing and particularly to FIGS. 1-3, one form of the safety goggles of this invention are shown enumerated generally as at 20. More particularly, the goggles include a one-piece frame 21 formed into a generally U-shape for fitting receipt on the face of a wearer over the eyes and extending to each temple. The frame has a pair of enlarged horizontally extending openings 22, 22', one for each eye, each of which broaden out vertically directly in front of each eye as at 23 and 24. The openings 22, 22' are also carefully dimensioned so as not to admit the smallest sized ball 25 of the sports in which the wearer may be engaged (e.g., squash, handball).

The frame members both above and below the openings 22, 22', include a plurality of spaced openings 26, thereby increasing the range of vision of the user.

Turning now particularly to FIG. 1, it is seen that soft resilient pads 27 and 28 are affixed to the inner frame surface opposite the respective temples of the wearer. Also, a further soft and resilient pad 29 is secured to the inner frame surface between the two openings 22, 22' for bearing against the nose. This pad 29 serves to make the goggles feel comfortable and additionally to hold the frame portions immediate the eye region in a slightly spaced relation therewith, thereby enhancing the protective feature of the goggles.

By the goggle construction shown in FIGS. 1-3 and just described, the wearer is protected against injury to the eye and immediately adjacent portions of the face and head by a game ball or racquet, while at the same time providing good visibility both horizontally by virtue of the elongated opening 22,22' and in a vertical direction as a result of the opening extensions 23 and 24.

Figure 4:
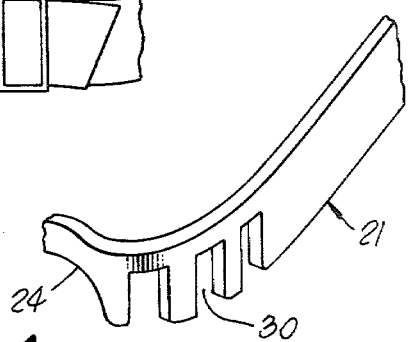
FIG. 4 is a perspective view of a modified frame.
Figure 5:
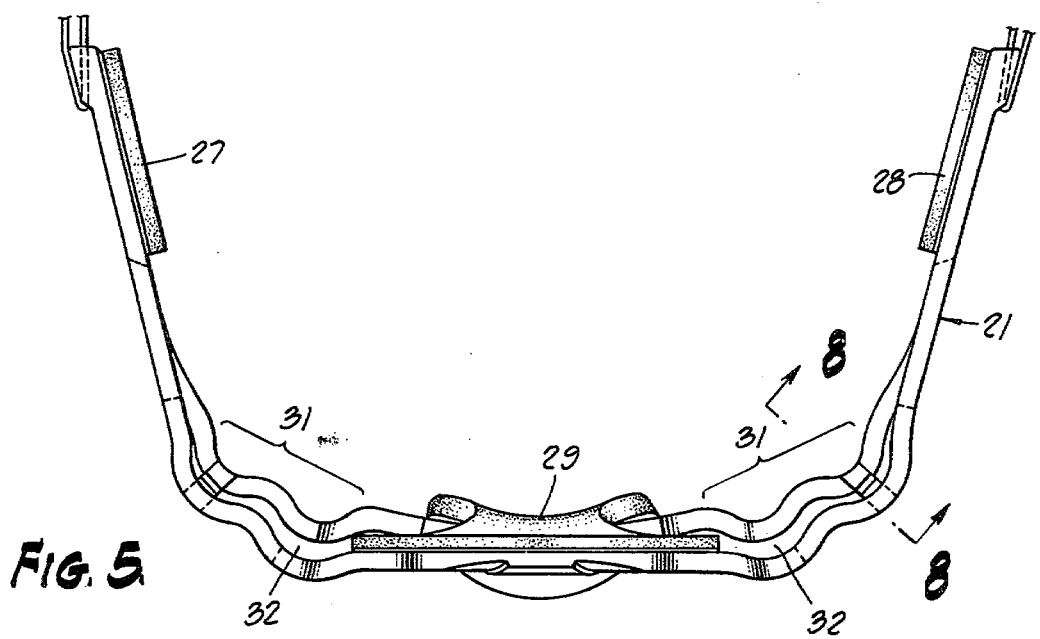
FIG. 5 is a perspective view of a still further embodiment.
Figure 6:
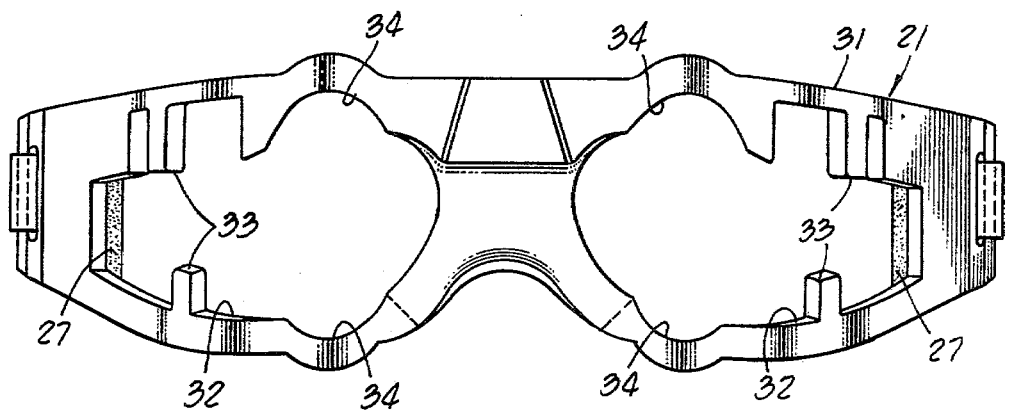
FIG. 6 is a front elevation and FIG. 7 is an end elevation of the goggles of FIG. 5.
Figure 7:
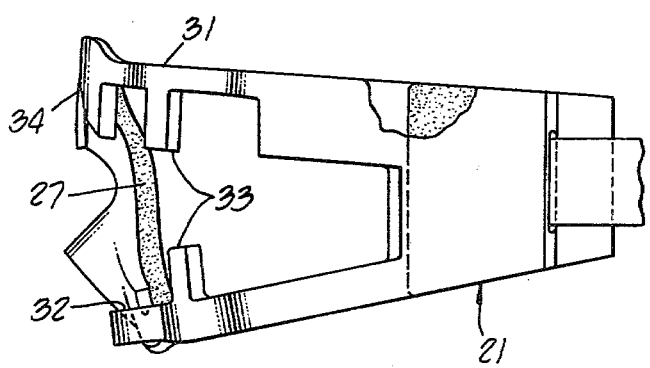
Figure 8:
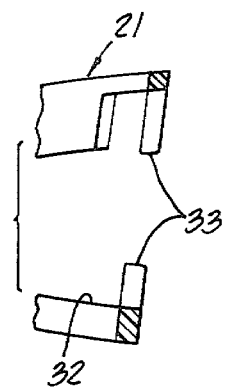
FIG. 8 is a sectional, elevational view taken along the line 8—8 of FIG. 5.
Figure 9:
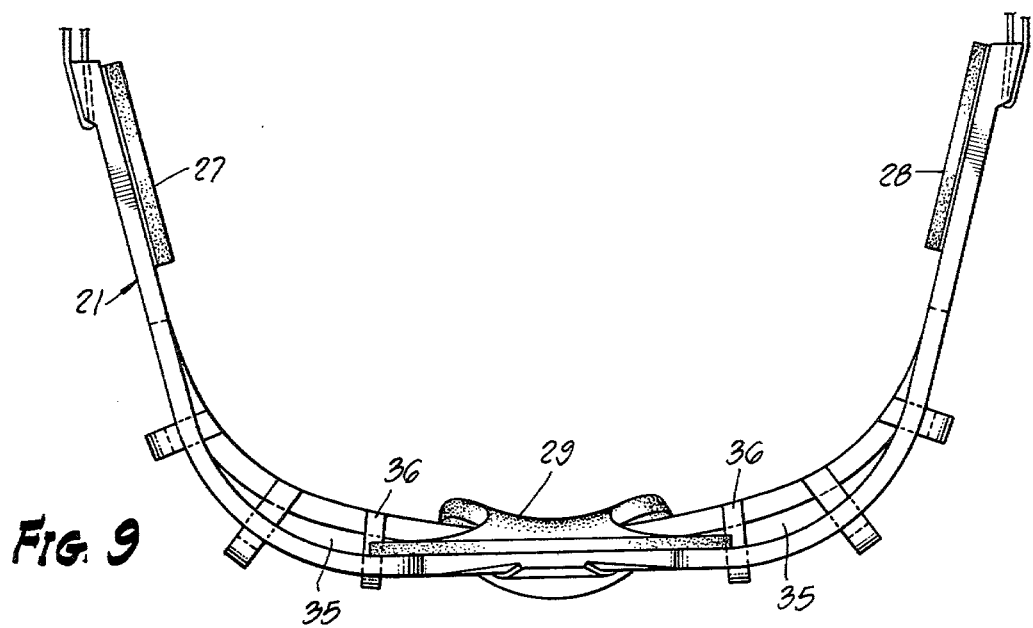
FIGS. 9, 10, 10a, 10b and 11 are a plan, front elevations and end elevation, respectively, of yet another version of this invention.
Figure 10:
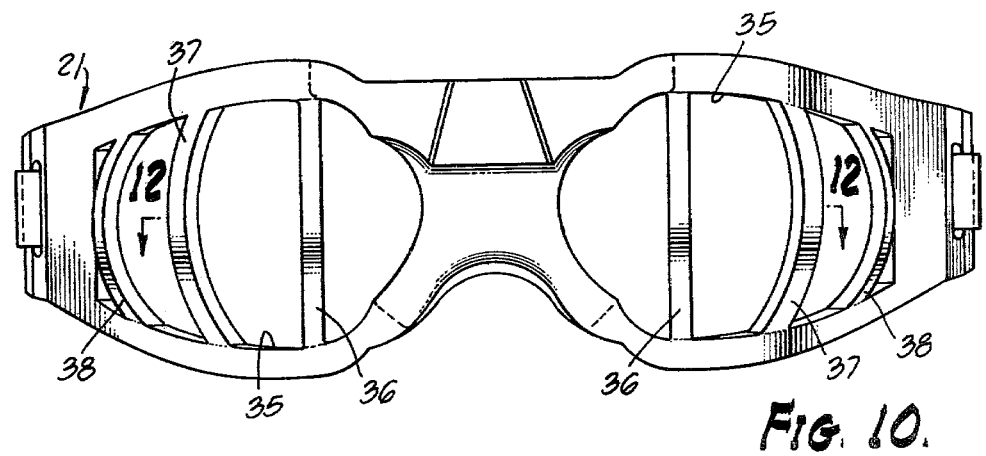

FIG. 4 shows a modified frame construction in accordance with another version of the invention. In this form, the frame portion lying between the openings 26 and openings 22, 22' has been removed, providing a toothed appearance. In this manner the frame openings to form the notches 30 provides the same amount of protection for the eye region, while increasing the visibility range.

In another embodiment, as depicted in FIGS. 5-8, the frame parts 21 extending generally horizontally from a point approximately directly in front of the eye to just beyond the eye socket are formed into an undulating configuration 31 with spaced convex portions separated by concave portions. In addition, the frame defines a generally horizontally extending opening 32 for each eye and having a notched or toothed edge 33 as seen best in FIG. 6 and similar to the toothed arrangement of FIG. 4 previously described. The elongated opening 32 is increased vertically in the region directly in front of the eye as at 34 to provide vertical visibility enhancement. As before, the dimensional extent of the opening 32 and the increased portions 34 thereof is such as to prevent any part of the game ball from passing therethrough and contacting the eye or immediately adjacent parts of the face of the wearer.

FIGS. 9 through 12 represent a still further modification in which the frames define elongated generally horizontal openings 35 for each eye and include a plurality of relatively thin, spaced, rod-like members 36, 37 and 38 extending vertically through the opening 35 with their respective ends affixed in the upper and lower frame parts. More particularly, the members 36 are located directly in front of the eye, while members 37 and 38 are spaced substantially therefrom.

It has been found that although a horizontal opaque member interposed in the field of view is a substantial obstruction to visibility of the wearer and impairing performance during the sport activity, vertical members 36–38 provide a very limited amount of obstruction and do not affect the concentration or general performance of the user while participating in sport.

Figure 11:
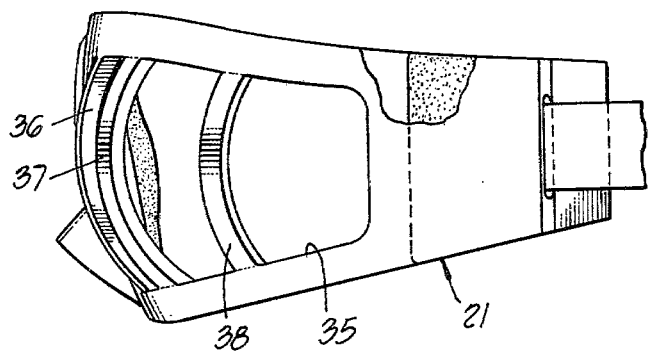
Figure 12:
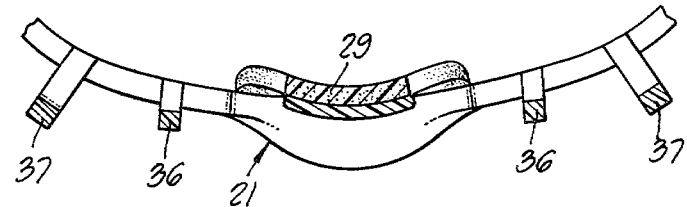
FIG. 12 is a plan, sectional view taken along line 12—12 of FIG. 10.

As is best seen in FIG. 11, the members 36–38 are preferably convexly curved outwardly away from the face of the wearer, however, it is considered within the spirit of the invention to have the members straight, although the curved construction serves to strengthen the members against any externally applied pressures, as well as to hold a game ball, racquet or the like at a greater distance from the eyes of the wearer in case of contact.

In the practice of this invention, there are provided safety goggles to be worn by a participant in a sport such as handball, squash, racquet ball, soccer, basketball or the like, which provide substantially complete visibility, are light weight and comfortable to wear, and yet provide complete safety against a game ball or other game implement striking the eye or adjacent parts of the face and injuring the wearer. Although other materials may be found satisfactory, it is contemplated that the described goggles can be most feasibly and practically manufactured of molded plastic.

Figure 10A:
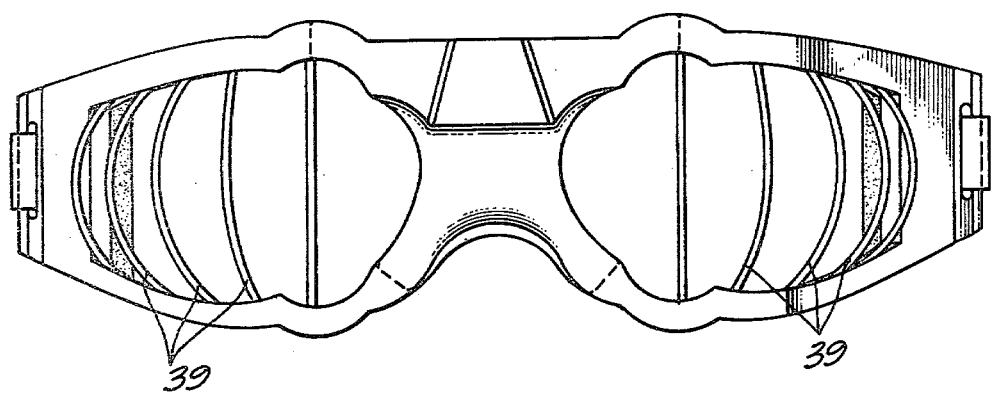

FIG. 10a shows a still further version of the invention which is generally similar to that depicted in FIGS. 9–12. Specifically, instead of the vertical members 36–38 which are generally rectangular in cross-section and contemplated as a one-piece molded construction with the frame, a plurality of relatively thin, spaced, wirelike elements 39 extend vertically across the frame opening. The ends of the wirelike elements are anchored within the frame walls defining the eye opening and the intermediate portions of the elements are curved convexly away from the face of the wearer. The elements 39 may be separate metal pieces having their ends embedded in the frame as described, or, optionally, may be one-piece molded with the frame.

Figure 10B:
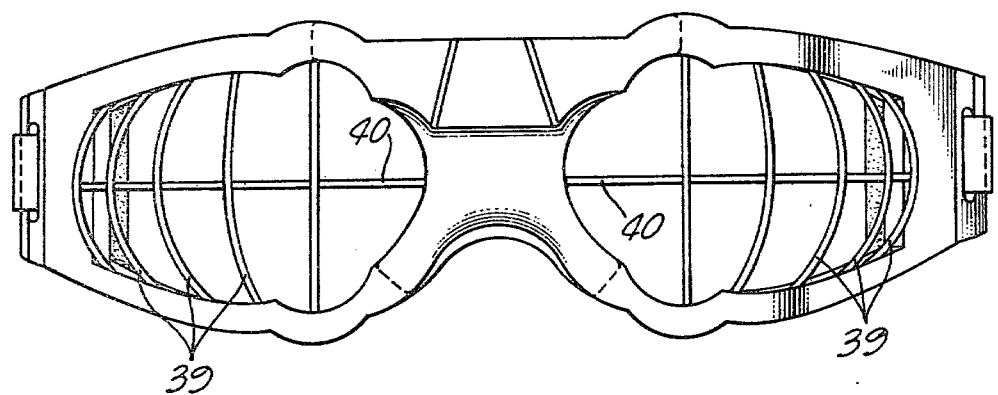

FIG. 10b is similar to FIG. 10a except that there is further provided a horizontally extending wirelike element 40 having each end anchored in the frame at the nosepiece and at the ends adjacent the temples of the wearer. The intermediate part of 40 is curved convexly away from the face of the wearer and supportively contacts the elements 39 in the preferred construction.

I claim:

1. Safety goggles for a sport using a ball, the goggles having a frame adapted for fitting receipt onto the face of a wearer and closely spaced therefrom, and including upper and lower frame parts defining an elongated generally horizontally extending opening opposite each eye of a vertical dimension at least equal to that of the eye pupil throughout its horizontal length, comprising:

each horizontally extending opening defined by the frame parts including a vertical extension directly in front of each eye, said horizontally extending openings and vertical extensions thereof being free of centrally located obstructions; and the upper and lower frame parts having a plurality of mutually spaced members integral with said frame parts and extending a limited extent into each horizontally extending opening outwardly of the vertical extension, said spaced members having their ends lying within the first and second openings spaced from one another;

each said horizontally extending opening and vertical extension thereof presenting a maximum circular open space less than the circular dimensions of said game ball.

2. Safety goggles as in claim 1, in which said goggles are constructed of a molded plastic material.

3. Safety goggles as in either of claims 1 or 2, in which the upper and lower frame parts defining the generally horizontally extending openings are formed into notches separated by projections directed to opposite frame parts.

* * * * *